US012571863B2

(12) United States Patent
Greiser et al.

(10) Patent No.: US 12,571,863 B2
(45) Date of Patent: Mar. 10, 2026

(54) LOCAL COIL AND MAGNETIC RESONANCE APPARATUS HAVING A SAFETY MECHANISM FOR PREVENTING A COLLISION WITH A PATIENT

(71) Applicants: Siemens Healthineers AG, Forchheim (DE); Dentsply Sirona Inc., York, PA (US); SIRONA Dental Systems GmbH, Bensheim (DE)

(72) Inventors: Andreas Greiser, Erlangen (DE); Johannes Ulrici, Darmstadt (DE); Florian Odoj, Veitshöchheim (DE); Marco Geißner, Estenfeld (DE)

(73) Assignees: Siemens Healthineers AG, Forchheim (DE); Dentsply Sirona Inc., York, PA (US); SIRONA Dental Systems GmbH, Bensheim (DE)

( * ) Notice: Subject to any disclaimer, the term of this patent is extended or adjusted under 35 U.S.C. 154(b) by 184 days.

(21) Appl. No.: 18/692,645

(22) PCT Filed: Aug. 22, 2022

(86) PCT No.: PCT/EP2022/073268
§ 371 (c)(1),
(2) Date: Mar. 15, 2024

(87) PCT Pub. No.: WO2023/041288
PCT Pub. Date: Mar. 23, 2023

(65) Prior Publication Data
US 2024/0377487 A1      Nov. 14, 2024

(30) Foreign Application Priority Data

Sep. 17, 2021    (DE) ..................... 10 2021 210 304.9
Feb. 28, 2022    (DE) ..................... 10 2022 202 052.9

(51) Int. Cl.
*G01R 33/34*      (2006.01)
*G01R 33/28*      (2006.01)
*A61B 5/055*      (2006.01)

(52) U.S. Cl.
CPC ..... *G01R 33/34007* (2013.01); *G01R 33/288* (2013.01); *G01R 33/34084* (2013.01); *A61B 5/055* (2013.01)

(58) Field of Classification Search
CPC ........... G01R 33/34007; G01R 33/288; G01R 33/34084; A61B 5/055
See application file for complete search history.

(56) References Cited

U.S. PATENT DOCUMENTS 5,307,806 A * 5/1994 Jones ............... G01R 33/34061
                                                        324/318
2012/0286784 A1    11/2012 Driemel
(Continued)

FOREIGN PATENT DOCUMENTS

DE      102011075454 B4      7/2016
WO      2023041289 A1      3/2023

OTHER PUBLICATIONS

Anonym: "Mandibula 15-Kanal Dental Spule—Noras MRI Products", Internet, 2017, Seiten 1-74, XP055980776, Gefunden im Internet: URL:https://docplayer.org/132670679-Mandibula-15-kanal-dental-spule-1-5t-si-t-si.html [gefunden am Nov. 14, 2022].
(Continued)

*Primary Examiner* — G.M. A Hyder
(74) *Attorney, Agent, or Firm* — Banner & Witcoff, Ltd.

(57)      ABSTRACT

A local coil including an antenna, base element, holding element, first and second guide mechanisms, and safety mechanism. The antenna receives high-frequency signals in a frequency range and power range of a magnetic resonance measurement and is mechanically connected to the holding element. The base element holds the holding element together with the antenna in a position for use on a diagnostically relevant body region of a patient. The first guide mechanism is mechanically connected to the base element and the holding element and positions the holding element variably relative to the base element. The second guide mechanism is mechanically connected to the holding element and the antenna and positions the antenna variably (Continued)

relative to the holding element. The safety mechanism prevents a collision between the antenna and the patient during a transfer of the holding element from an open position into a closed position using the first guide mechanism.

15 Claims, 7 Drawing Sheets

(56)  References Cited

U.S. PATENT DOCUMENTS

| | | | | |
|---|---|---|---|---|
| 2013/0218000 A1* | 8/2013 | Coppens | ............... | A61B 5/708 |
| | | | | 600/411 |
| 2014/0148686 A1* | 5/2014 | Thevathasan | .......... | A61B 5/055 |
| | | | | 600/415 |
| 2014/0187910 A1* | 7/2014 | Culver | .................. | A61B 5/055 |
| | | | | 600/411 |

OTHER PUBLICATIONS

Jan. 13, 2023 (PCT) International Search Report and Written Opinion.

Anonymous, "Mandibula 15-Channel Dental Coil—Noras MRI Products", Online 2017, pp. 1-74, Internet Retrieved from: URL:https://docplayer.org/132670679-Mandibula-15-kanal-dental-wickel-1-5t-si-t-si.html XP055980776[found on Nov. 14, 2022] (w/English Translation).

* cited by examiner

LOCAL COIL AND MAGNETIC RESONANCE APPARATUS HAVING A SAFETY MECHANISM FOR PREVENTING A COLLISION WITH A PATIENT

TECHNICAL FIELD

The disclosure relates to a local coil comprising at least one antenna, a base element, a holding element, a first guide mechanism, and a second guide mechanism, wherein the at least one antenna is designed to receive high-frequency signals in a frequency range and power range of a magnetic resonance measurement and wherein the at least one antenna is mechanically connected to the holding element, wherein the base element is designed to hold the holding element together with the at least one antenna in a position appropriate for use on a diagnostically relevant body region of a patient, wherein the first guide mechanism is mechanically connected to the base element and the holding element and is designed to position the holding element variably relative to the base element and wherein the second guide mechanism is mechanically connected to the holding element and the at least one antenna and is designed to position the at least one antenna variably relative to the holding element. The disclosure further relates to a magnetic resonance apparatus comprising a local coil according to the disclosure.

BACKGROUND

Diseases of the teeth and the periodontium, such as, e.g., caries or periodontitis, are typically diagnosed currently using X-ray-based imaging methods. Conventional or digital X-ray projection methods, as well as recently also three-dimensional X-ray methods, are primarily used in this case. One example of a three-dimensional X-ray method is digital volume tomography, which can be used for imaging teeth and the viscerocranium.

A major disadvantage of X-ray methods is the need to use ionizing radiation for the imaging process. Magnetic resonance tomography is representative of an imaging method that avoids ionizing rays. This typically provides a better soft tissue contrast than X-ray methods and supports three-dimensional imaging of an examination subject as standard. Furthermore, magnetic resonance tomography enables imaging of cysts as well as detection of a degradation of dentin before this becomes detectable by means of an X-ray method. Magnetic resonance tomography, therefore, represents a potential alternative to known X-ray methods for the imaging of a dental region and/or a jaw region as well as for the diagnosis of dental diseases of the examination subject.

Magnetic resonance tomography is a well-known imaging modality by means of which magnetic resonance images of an internal region of the examination subject can be generated. When a magnetic resonance imaging procedure is carried out, the examination subject is normally positioned in a strong, static, and homogeneous basic magnetic field (B0 magnetic field) of a magnetic resonance apparatus. The basic magnetic field can exhibit magnetic field strengths of 0.2 tesla to 7 tesla such that nuclear spins of the examination subject align themselves along the basic magnetic field. In order to trigger so-called nuclear spin resonances, high-frequency signals, also known as radiofrequency excitation pulses (B1 magnetic field), are radiated into the examination subject. Each excitation pulse causes a magnetization of certain nuclear spins of the examination subject to deviate from the basic magnetic field by an amount that is also known as the flip angle. An excitation pulse can, at the same time, have a magnetic alternating field at a frequency that corresponds to the Larmor frequency for the respective static magnetic field strength. The excited nuclear spins can exhibit a rotating and decaying magnetization (nuclear spin resonance), which can be captured as a magnetic resonance signal by means of special antennas. Magnetic gradient fields can be superimposed on the basic magnetic field for spatial encoding of the nuclear spin resonances of the examination subject.

The received magnetic resonance signals are typically digitized and stored as complex values in a k-space matrix. This k-space matrix can be used as a basis for reconstructing magnetic resonance images as well as for determining spectroscopic data. A magnetic resonance image is typically reconstructed by means of a multidimensional Fourier transform of the k-space matrix.

Owing to the avoidance of ionizing radiation, magnetic resonance tomography is suitable in particular for continuous diagnostic monitoring of dental disease and/or of dental development as part of a longitudinal imaging study. In longitudinal imaging studies, multiple imaging examinations are typically performed in order to determine a progression of a disease or a success of a therapeutic treatment over a predetermined period of time. However, diagnostically relevant areas of the jaw region of a patient, such as, e.g., an oral cavity, a set of teeth, a dental arch, or a tooth, provide only a small volume that is available for generating magnetic resonance signals. Furthermore, conventional volume and surface coils, such as, e.g., head coils and lay-on coils, are placed at a relatively great distance from the jaw region of the patient. However, a great distance can increase a signal-to-noise ratio of captured magnetic resonance signals and consequently reduce the quality of magnetic resonance images of the teeth of the patient reconstructed therefrom. For a clinical application, it is furthermore advantageous if the coil can be positioned repeatedly and in a time-efficient manner in immediate proximity to the jaw region of the patient. Owing to the immediate proximity to the patient, safety aspects, in particular, must also be taken into consideration due to varying patient anatomies.

SUMMARY

It is, therefore, an object of the invention to provide a local coil that enables high-quality magnetic resonance images to be acquired without compromising the safety of the patient.

The local coil according to the disclosure comprises at least one antenna, a base element, a holding element, a first guide mechanism, a second guide mechanism, and a safety mechanism.

The at least one antenna is designed to receive radiofrequency signals in a frequency range and power range of a magnetic resonance measurement. An antenna can constitute a coupling element between electromagnetic waves conducted in signal conductors and unconducted electromagnetic waves, i.e., waves located in a free space. The at least one antenna is embodied in particular to receive electromagnetic waves in the region of a magnetic resonance frequency of a magnetic-resonance-active atomic nucleus. Electromagnetic waves relevant to magnetic resonance measurements can represent radiofrequency signals (magnetic resonance signals) comprising frequencies between 1 and 500 MHz, preferably between 10 and 300 MHz. The magnetic resonance signals of typical atomic nuclei to be examined can exhibit a low power of a few microwatts up to several milliwatts.

A signal conductor is preferably an electrically conducting wire. The wire of the signal conductor can have an oval or polygonal cross-section and be suitable for continuously transmitting the above-stated power levels. It is also conceivable that the signal conductor is implemented as a conductor track on a printed circuit board and has an approximately rectangular cross-section. The signal conductor can consist of copper. However, other electrically conducting metals, such as, e.g., gold, aluminum, and the like, are also conceivable.

The local coil according to the disclosure can, of course, comprise more than one antenna. In this case the antennas can be arranged spaced apart from one another, adjacent to one another or partially overlapping. Further, the antennas can be arranged in the form of a grid or matrix.

In a preferred variant, the local coil has a number of antennas that are embodied to receive magnetic resonance signals from the diagnostically relevant body region, in particular a head region or a jaw region of the patient. The at least one antenna can be mechanically connected to a carrier structure and be carried or retained by the same. It is also conceivable for the at least one antenna to be integrated or embedded into the carrier structure. The carrier structure can comprise a material that is embodied to provide contact protection for the patient and/or to be shaped to conform to a contour of the diagnostically relevant body region of the patient.

It is conceivable that the local coil according to the disclosure has at least one antenna that is configured to transmit a radiofrequency signal in a direction of the examination subject, such as, e.g., into a jaw region of the patient. Depending on the basic magnetic field of a magnetic resonance apparatus, the radiofrequency signal transmitted by the at least one antenna can lie for example in a power range of a few watts up to several kilowatts. The radiofrequency signal transmitted by the at least one antenna can represent in particular a B1 magnetic field. A part of the local coil having the at least one antenna can, for example, represent a transmit unit of the local coil.

The at least one antenna is mechanically connected to the holding element. The holding element can represent an arbitrary carrier element that is embodied to maintain the at least one antenna in a predetermined position relative to the diagnostically relevant body region of the patient. Preferably, the holding element is embodied to position and/or align the at least one antenna roughly relative to the patient. A precise positioning and/or alignment of the at least one antenna relative to the diagnostically relevant body region of the patient is preferably accomplished by means of the second guide mechanism.

The base element is embodied to keep the holding element together with the at least one antenna in a position appropriate for use on a diagnostically relevant body region of a patient. For this purpose, the base element is preferably mechanically connected to a component of a magnetic resonance apparatus, such as, e.g., a patient table and/or a patient support and positioning apparatus. The base element may, for example, comprise a positioning unit that is embodied to position the base element and/or the holding element together with the at least one antenna relative to the magnetic resonance apparatus and/or the patient. The base element can be moved to a position appropriate for use on the patient such that it flanks the diagnostically relevant body region of the patient on two opposite sides or at least partially encloses said body region. Preferably, the base element is embodied to reduce or minimize a movement of the diagnostically relevant body region of the patient during an imaging examination.

The first guide mechanism is mechanically connected to the base element and the holding element and is embodied to position the holding element variably relative to the base element. The first guide mechanism may encompass any desired mechanical principle that permits a movement of the holding element relative to the base element. The first guide mechanism preferably comprises a joint, in particular a pivoting or hinged mechanism, a rail system, a linear guide, or the like. The first guide mechanism is preferably designed to allow a particularly simple and/or time-efficient transfer of the holding element from an open position to a closed position.

The second guide mechanism is mechanically connected to the holding element and the at least one antenna and is embodied to position the at least one antenna variably relative to the holding element. The second guide mechanism is preferably embodied to enable a precise positioning and/or alignment of the at least one antenna relative to the diagnostically relevant body region. For this purpose, the second guide mechanism can comprise, e.g., a screw-like mechanism, a clamping mechanism, a serrated grid mechanism, a telescopic system, a rail system, as well as a joint, a hinge, and/or a comparable mechanical principle.

In particular, the first guide mechanism and/or the second guide mechanism provide a guide for the holding element and/or the at least one antenna. This can mean that a movement of the holding element by means of the first guide mechanism and/or a movement of the at least one antenna by means of the second guide mechanism are/is limited to a predetermined number of spatial directions and/or directions of rotation. For example, the positioning of the holding element relative to the base element by means of the first guide mechanism can be limited to a movement of the holding element along two opposite directions of rotation. On the other hand, the positioning of the at least one antenna relative to the holding element can be limited to a movement along a straight line, a plane, a straight line and a plane, as well as along two planes, in particular two orthogonal planes.

The safety mechanism is embodied to prevent a collision between the at least one antenna and the patient, in particular, the diagnostically relevant body region of the patient, when the holding element is moved from an open position to a closed position by means of the first guide mechanism. The safety mechanism is preferably embodied to limit a movement of the holding element relative to the base element and/or to make or initiate an adjustment of a position of the at least one antenna relative to the holding element. It is conceivable that the safety mechanism is embodied to prevent a collision between the at least one antenna and the diagnostically relevant body region of the patient automatically, in particular also in the event of an operating error by a user. The safety mechanism can furthermore be configured to protect against or prevent a plurality of scenarios involving a potential incorrect use of the local coil that results in a collision of the at least one antenna with the diagnostically relevant body region.

A collision may be characterized by an unwanted contact or coming together of the at least one antenna with the diagnostically relevant body region of the patient. A collision may presuppose a movement of the at least one antenna in the direction of the diagnostically relevant body region of the patient. It is conceivable, in particular, that the collision comprises a contact, an action of force, and/or a transmission of force between the one antenna and the diagnostically relevant body region of the patient. In this context, however, only those movements, contacts, and/or actions of force caused by a movement of the holding element by means of the first guide mechanism are to be considered as a collision. A contact between the at least one antenna and the diagnostically relevant body region which is produced solely by a movement of the at least one antenna by means of the second guide mechanism is therefore regarded as wanted and does not fall within the above-stated definition of a collision.

An open position of the holding element may be characterized by a maximum or predetermined deflection of the holding element relative to the base element by means of the first guide mechanism. The open position may, in particular, constitute a "loading position" which allows a positioning of the diagnostically relevant body region of the patient in a position appropriate for use relative to the base element. In contrast, a closed position of the holding element may be characterized by a minimum deflection of the holding element relative to the base element by means of the first guide mechanism. The closed position may, in particular, constitute an "examination position" that is characterized by a position of the holding element appropriate for use relative to the diagnostically relevant body region of the patient during a magnetic resonance measurement. Transferring the holding element from the open position to the closed position may, in particular, comprise a bringing together of the holding element and the base element. It is conceivable that when said two elements are brought together by means of the first guide mechanism, the holding element is moved or deflected in a direction facing toward the base element.

By providing the local coil according to the disclosure it is possible to avoid a risk of a collision between the at least one antenna and the diagnostically relevant body region of the patient when positioning the holding element and/or the at least one antenna in the position appropriate for use on the patient. Furthermore, a level of safety in the handling of the local coil according to the disclosure can be increased by means of a safety mechanism according to the disclosure. As a result, a positioning of the local coil on the diagnostically relevant body region can advantageously be accomplished also by less qualified staff.

In a variant of the local coil according to the disclosure, the safety mechanism is designed to limit a movement of the holding element by means of the first guide mechanism when the holding element is transferred from the open position to the closed position in accordance with a safety position of the at least one antenna relative to the holding element.

The safety mechanism is preferably embodied to prevent or block a movement of the holding element relative to the base element in the direction of the base element if the position of the at least one antenna relative to the holding element exceeds a predetermined limit value. Limiting the movement of the holding element by means of the first guide mechanism may signify a cushioning, but, in particular, an inhibiting or blocking, of the movement of the holding element relative to the base element. The predetermined limit value may be characterized, for example, by a safety position of the at least one antenna relative to the holding element. The safety position is preferably defined by a predetermined distance of a first reference point of the at least one antenna from a second reference point of the holding element. For example, the predetermined distance of the first reference point of the at least one antenna from the second reference point of the holding element can be chosen such that a collision of the at least one antenna with a patient when the holding element is transferred from the open position to the closed position is statistically improbable or can be ruled out.

In a preferred variant, the first guide mechanism is mechanically coupled to the second guide mechanism in such a way that a movement of the holding element in the direction of the base element is prevented when the predetermined limit value is exceeded.

By means of the safety mechanism according to the disclosure, a bringing together of the holding element and the base element can advantageously be avoided if the current position of the at least one antenna relative to the holding element deviates from the safety position of the at least one antenna relative to the holding element. As a result, a risk of an injury to the patient when the holding element and the base element are brought together can advantageously be prevented.

In a preferred variant of the local coil according to the disclosure, the safety mechanism has a first latching component, which is designed to engage in a second latching component of the first guide mechanism and prevent the holding element from being transferred from the open position to the closed position.

In the course of the following explanations, it is assumed for simplicity that the second latching component is embodied as a serrated profile. The first latching component can consequently be embodied as an arbitrary latching element that is designed to engage mechanically with the serrated profile in order to prevent or block a movement of the latching element relative to the serrated profile in at least one spatial direction. However, it is equally conceivable that the first latching component is embodied as a serrated profile. In this case the second latching component can constitute an arbitrary latching element that is embodied to engage mechanically with the serrated profile in order to prevent or block a movement of the latching element relative to the serrated profile in at least one spatial direction.

The latching element is preferably embodied to engage in a positive-locking and/or force-fitting manner with the serrated profile of the first guide element in order to limit or prevent the movement of the holding element relative to the base element in at least one spatial direction. The latching element and the serrated profile can be embodied in such a way that the latching element is able to pass the serrated profile in a first movement direction, such as, e.g., an opening movement of the holding element (in other words, a movement of the holding element in an opposite direction to the base element), whereas in a second movement direction, such as, e.g., a closing movement of the holding element (in other words, a movement of the holding element in the direction of the base element), the latching element engages in the serrated profile and prevents a further movement. The latching element can be mounted on an elastic element, such as, e.g., a mechanical spring or an elastomer. It is equally conceivable that the latching element itself comprises an elastic material and/or is (elastically) deformable.

The first latching component is mechanically connected to a retaining element, the first latching component being mechanically separable from the second latching component of the first guide mechanism by means of the retaining element in order to enable the holding element to be transferred from the open position to the closed position.

The retaining element can comprise a mechanism that is embodied to change a position, a shape, and/or an orientation of the latching element and/or of the elastic element in order to separate the latching element manually or automatically from the serrated profile of the first guide mechanism. The mechanism can comprise, in particular, a clasping mechanism, a pulling mechanism, a spring mechanism, a bending mechanism, and/or an actuating mechanism which are embodied as part of the latching element and/or are mechanically coupled to the latching element. For example, the latching element can be mounted on the retaining element in such a way that the latching element can be separated from the serrated profile as a function of a predetermined movement and/or a predetermined action of the force of the retaining element onto the latching element. The retaining element may also comprise an elastic element according to an above-described variant or be embodied as such an element.

Preferably, the retaining element is mechanically coupled to the second guide mechanism such that the predetermined action of force and/or the predetermined movement of the retaining element is caused or triggered by the movement of the at least one antenna relative to the holding element.

In a further variant, the retaining element can be actuated manually by a user and/or automatically by means of an electrical circuit. Because it is possible to actuate the retaining element manually, a detent blocking the movement of the holding element in the direction of the base element can advantageously be released intentionally by a user. Actuating the retaining element by means of an electrical circuit advantageously enables a release of the detent to be automated. For example, the position of the at least one antenna relative to the holding element can, in this case, be monitored by means of one or more suitable sensors.

In a variant of the local coil according to the disclosure, the first latching component is mechanically coupled to the second guide mechanism by means of the retaining element. The first latching component can be mechanically separated from the second latching component of the first guide mechanism by means of a movement of the at least one antenna to a predetermined position relative to the holding element by means of the second guide mechanism in order to enable the holding element to be transferred from the open position to the closed position.

The retaining element can be embodied to change a position, a shape, and/or an orientation of the latching element in order to separate the latching element mechanically from the serrated profile of the first guide mechanism. For this purpose, the retaining element can be embodied in particular as an elastic element according to an above-described variant. Preferably, the retaining element is mechanically coupled to the second guide mechanism in such a way that the latching element is separated automatically from the serrated profile of the first guide mechanism when a predetermined position of the at least one antenna relative to the holding element is present.

A latching element can represent a particularly easy-to-implement and/or cost-effective solution for the safety mechanism according to the disclosure. Furthermore, a failsafe and/or robust solution for preventing a collision of the at least one antenna with the diagnostically relevant body region of the patient can be provided by means of the latching element.

In a variant of the local coil according to the disclosure, the safety mechanism is mechanically coupled to the first guide mechanism and the second guide mechanism and is embodied to transfer the at least one antenna into a safety position relative to the holding element using a kinematic energy of a movement of the holding element relative to the base element.

The safety mechanism is preferably embodied as a mechanical coupling between the first guide mechanism and the second guide mechanism. Such a mechanical coupling may, in particular, comprise a set of gears having one or more gear bodies and/or shafts. The mechanical coupling preferably comprises a no-load or decoupling mechanism, which is embodied to limit the transfer of the at least one antenna into the safety position with respect to the holding element to a closing movement or an opening movement of the holding element. The decoupling mechanism can furthermore be embodied to transfer the at least one antenna into a predetermined relative position with respect to the holding element by means of the safety mechanism during the opening movement or closing movement.

The predetermined relative position of the at least one antenna may be characterized, for example, by a maximum deflection or a maximum distance of the at least one antenna with respect to the base element. In this case the at least one antenna may be located in a stop or end position relative to the holding element in a direction facing away from the base element. However, it is also conceivable that the predetermined relative position is characterized by a permissible deflection of the at least one antenna with respect to the holding element in the direction of the base element. In this case, the permissible deflection is preferably chosen such that a collision of the at least one antenna with the diagnostically relevant body region during a closing movement of the holding element is statistically improbable or can be ruled out. The predetermined relative position of the at least one antenna with respect to the holding element can in particular coincide with the safety position of the at least one antenna.

By providing a mechanical coupling for transferring the at least one antenna into the predetermined position relative to the holding element using a kinematic energy of the relative movement of the holding element and of the base element, it is advantageously possible to dispense with an additional drive and/or an additional operating step for positioning the at least one antenna in the predetermined position relative to the holding element.

In a further variant of the local coil according to the disclosure, the second guide mechanism has a clamping element that is embodied to be elastically deformed following a movement of the at least one antenna relative to the holding element in the direction of the base element and to transmit a force acting opposite to the movement onto the at least one antenna. A clamping element can represent an arbitrary elastic element, such as, e.g., a mechanical spring, a rubber band and/or a body made of an elastic material. An elastic material may include a synthetic or natural elastomer, such as, e.g., rubber or a synthetic polymer. The clamping element may in particular be fabricated from a plastic or a metal.

The clamping element preferably has a mechanical connection to the at least one antenna and the holding element. The clamping element can be connected to the at least one antenna and the holding element in such a way that the clamping element is elastically deformed in the course of a movement of the at least one antenna relative to the holding element in the direction of the base element. As a result of the elastic deformation, elastic restoring forces can be built up in the clamping element which act in the opposite direction to the movement direction of the at least one antenna.

The safety mechanism has a first latching component which is mechanically connected to the at least one antenna and is embodied to engage in a second latching component of the second guide mechanism and counteract the force of the clamping element. In this case, the first latching component and the second latching component can be implemented according to an above-described variant.

The first latching component is mechanically coupled to the first guide mechanism, the first latching component being mechanically separable from the second latching component of the second guide mechanism by means of a predetermined movement of the holding element relative to the base element in order to enable a deflection of the at least one antenna in a direction facing away from the base element by means of the clamping element. The mechanical coupling of the first guide mechanism to the latching element may be embodied, for example, as a retaining element according to an above-described variant. Preferably, such a retaining element is embodied to separate the latching element from the serrated profile of the second guide mechanism during an opening movement of the holding element, the at least one antenna being transferred into a starting position by means of the elastic restoring forces of the clamping element.

Using the same mechanical principle, the clamping element and the mechanical coupling may alternatively be embodied also to return the at least one antenna into a starting position when a closing movement of the holding element is performed, i.e., when the holding element is moved relative to the base element in the direction of the base element.

By providing a clamping element and a corresponding safety mechanism it can advantageously be ensured that the at least one antenna is located in a starting position following an opening movement of the holding element. Furthermore, a purely mechanical solution for the automated resetting of the at least one antenna advantageously enables an additional energy requirement for electrically driven components to be avoided.

In a further variant of the local coil according to the disclosure, the safety mechanism comprises an actuating element that is embodied to transmit a force onto the at least one antenna in order to deflect the at least one antenna relative to the holding element in a direction facing away from the base element. The actuating element can be connected for example to a pneumatic, hydraulic and/or electric drive which is embodied to transfer the actuating element and the at least one antenna into a starting position and/or into the predetermined position relative to the holding element. The actuating element is preferably embodied to transport or move the at least one antenna along a movement trajectory predefined by the second guide element in a direction facing away from the base element.

The local coil further comprises a locking element that is mechanically coupled to the first guide element and is embodied to interrupt the transmission of the force onto the at least one antenna by the actuating element when the base element and the holding element are located in a predetermined relative position. The locking element may be embodied, for example, as a stop element, such as, e.g., a pin, a bolt, a latching element, a plate, but also a fixture, a valve, or the like. The locking element can in particular be designed to interrupt an action of force of the drive exerted onto the actuating element.

It is equally conceivable that the locking element is embodied to enable a movement of the at least one antenna along the movement trajectory predefined by the second guide element. The mechanical coupling between the locking element and the first guide mechanism may be embodied according to an above-described variant. Preferably, the mechanical coupling is embodied to transfer the locking element into an open or closed position when the holding element is guided into a closed position relative to the base element. In this case, the deflection of the at least one antenna or the action of force of the actuating element onto the at least one antenna can be interrupted by the transfer of the locking element into the open or closed position.

In an alternative variant of the local coil according to the disclosure, the safety mechanism comprises an actuating element, the actuating element being embodied to transmit a force onto the holding element in order to limit a movement of the holding element relative to the base element and/or to deflect the holding element in a direction facing away from the base element. The actuating element and the drive may be implemented according to an above-described variant. In particular, the drive may be embodied as a pneumatic, hydraulic, or electric drive.

The local coil further comprises a locking element that is mechanically coupled to the second guide element and is embodied to interrupt the transmission of the force onto the holding element by the actuating element when the at least one antenna is located in a predetermined position relative to the holding element. The predetermined position of the at least one antenna relative to the holding element is preferably characterized by a maximum distance of the at least one antenna relative to the base element and/or a maximum deflection of the at least one antenna in a direction facing away from the base element with respect to the holding element.

In a variant of the local coil according to the disclosure, the actuating element has a fluidic connection to a pneumatic and/or hydraulic drive, the locking element being embodied to interrupt the fluidic connection between the actuating element and the pneumatic and/or hydraulic drive. The locking element can be embodied as a valve, in particular a 3-way valve, for example.

In a variant, the valve is designed to interrupt the action of force of the actuating element onto the at least one antenna when the holding element is located in a closed position relative to the base element. In this case, the mechanical coupling between the first guide mechanism and the valve can be embodied, in particular, as an actuating drive for the valve. The valve can be transferred by means of the actuating drive into a configuration that interrupts or opens the fluidic connection to the pneumatic or hydraulic drive.

In an alternative variant, the valve is embodied to interrupt the action of force of the actuating element onto the holding element when the at least one antenna is located in the predetermined position relative to the holding element.

Providing an actuating element according to an above-described variant advantageously enables pneumatic and/or hydraulic systems that typically are already present in an examination room of a magnetic resonance apparatus to be used for implementing the safety mechanism. Furthermore, fluid lines, in particular fluid lines of pneumatic systems, can be manufactured from materials that exhibit a minimal or negligible interaction with magnetic and/or radiofrequency fields. Advantageously, such fluid lines can also be used in a patient receiving zone or an image acquisition region of the magnetic resonance apparatus without affecting the quality of acquired magnetic resonance images.

In a further variant of the local coil according to the disclosure, the safety mechanism comprises an actuating element having a drive, the actuating element being mechanically connected to the at least one antenna or the holding element and the drive being embodied to deflect the at least one antenna or the holding element by means of the actuating element in a direction facing away from the base element as a function of a control signal. The drive is preferably positioned outside the patient receiving zone or the image acquisition region of the magnetic resonance apparatus. The drive can be connected to the actuating element by means of a fluid line or alternatively also an electrical and/or mechanical coupling. It is conceivable for the drive to be integrated in the local coil and/or the patient support and positioning apparatus.

The safety mechanism may further comprise a control unit that is embodied to output or transmit the control signal to the drive. It is conceivable that the control unit is embodied to provide the control signal as a function of an open position and/or a closed position of the holding element and the base element. For this purpose, the control unit can maintain a signal connection to a sensor that is embodied to determine a position of the holding element relative to the base element, in particular, an open position and/or a closed position of the holding element. In a simple example, the sensor can be embodied as a switch, a contact, a relay, or the like. Such sensors are suitable, in particular, for detecting a presence of the holding element in an end position or stop position relative to the base element. However, the sensor can also comprise more complex measurement methods, such as, e.g., a laser distance measurement between the holding element and the base element or a determination of a deformation of a fiberoptic sensor when the closed position and/or open position of the holding element are/is reached. The sensor can be suitable for determining a finite number of predetermined positions of the holding element relative to the base element. However, it is also conceivable that the sensor is embodied to determine the position of the holding element relative to the base element continuously or in discrete time increments.

In a variant, the control unit includes a signal connection to a control unit and/or a computing unit of the magnetic resonance apparatus. It is equally conceivable that the control unit coincides with the control unit of the magnetic resonance apparatus or is integrated in the same. The control signal can accordingly be output as a function of a sensor of the magnetic resonance apparatus and/or in accordance with a parameter of a magnetic resonance measurement. A parameter of a magnetic resonance measurement can, for example, comprise an imaging parameter, but also an arbitrary parameter that characterizes a workflow or a progress of the magnetic resonance measurement.

By providing an electric drive according to the disclosure and a control unit it is advantageously possible to automate measures for preventing the collision of the at least one antenna by means of the safety mechanism. This advantageously enables a risk of an error by a user operating the local coil according to the disclosure to be reduced or avoided altogether.

In a variant, the first guide mechanism and/or the second guide mechanism are/is embodied as a linear guide, a telescopic guide, a joint, a hinge, or a push-fit system. A push-fit system may comprise a plurality of components that are available separately from one another in a disassembled or dismantled state. In a preferred variant, the base element is mechanically connected to the patient support and positioning apparatus by means of a positioning unit, wherein the holding element together with the at least one antenna can be connected to the base element as guidable or pluggable in a substantially vertical direction. However, the holding element may also be pluggable or guidable in a substantially horizontal direction or in a direction inclined to the vertical direction relative to the base element.

Basically, the first guide mechanism and/or the second guide mechanism may comprise an arbitrary mechanism that limits a movement of the holding element relative to the base element and/or of the at least one antenna relative to the holding element to one or more predetermined movement trajectories.

In a preferred variant of the local coil according to the disclosure, the first guide mechanism has a pivoting mechanism, the holding element being pivotable by means of the pivoting mechanism through a maximum angle relative to the base element.

The pivoting mechanism may comprise for example a hinge, a joint, a pivot bearing, a slide bearing, an antifriction bearing, a roller bearing, and/or an arbitrary other mechanism that is embodied to pivot the first element and/or the second element at an angle relative to the retainer and/or the patient support and positioning apparatus. When the local coil is positioned in a manner appropriate for use on the patient, the first element and/or the second element can preferably be pivoted along a sagittal plane of the patient. However, it is also conceivable that the holding element is pivotable approximately parallel to a frontal plane of the patient. During the pivoting movement, the holding element and/or the at least one antenna can follow a segment of an arc that is determined by the pivoting mechanism. It is conceivable that the pivoting mechanism is incorporated in the base element and/or integrated into the same according to an above-described variant.

In a preferred variant, the pivoting mechanism has a latching element and a serrated profile. According to an above-described variant, the latching element can be embodied to engage in the serrated profile and prevent a pivoting of the holding element along the direction of the base element. The latching element is preferably mechanically coupled to the second guide mechanism. The mechanical coupling can be embodied in such a way that the latching element is separated from the serrated profile when the at least one antenna is moved into a predetermined position relative to the holding element by means of the second guide mechanism.

The open position is characterized by the maximum angle between the base element and the holding element. The maximum angle is chosen such that the head of the patient can be positioned unobstructed in a position appropriate for use relative to the local coil.

Depending on the configuration of the magnetic resonance apparatus and/or the patient support and positioning apparatus, the maximum angle can range between 60° and 90°, 90° and 180° or 180° and 270°. In magnetic resonance apparatuses in which the patient assumes a standing or sitting posture during the magnetic resonance measurement, the maximum angle preferably ranges between 60° and 90°. However, greater values of the maximum angle are also conceivable. In conventional magnetic resonance apparatuses having a patient table, the maximum angle is preferably less than 180°.

By providing a pivoting mechanism it is possible for the holding element to be positioned in a particularly time-efficient way on the diagnostically relevant body region of the patient and to be removed again completely from an access area of the patient to the patient support and positioning apparatus. This advantageously allows the time required for positioning the local coil in a manner appropriate for use on the diagnostically relevant body region of the patient to be reduced.

In a further variant, the local coil according to the disclosure has a second antenna, the second antenna being mechanically connected to the base element. The second antenna may be embodied analogously to the at least one antenna. It is conceivable that the second antenna is electrically separated from the at least one antenna or electrically connected to the at least one antenna.

When the patient is positioned in a manner appropriate for use relative to the base element, the second antenna is positioned on a side of the patient facing away from the at least one antenna. The second antenna is preferably integrated or embedded in the base element. It is equally conceivable that the second antenna is connected to the base element in a positive-locking, force-fitting, and/or material-to-material bonded manner.

In a preferred variant, the local coil according to the disclosure is embodied as a head coil or a dental coil. The base element of the dental coil is preferably embodied to accommodate the head of the patient. When the patient is positioned in a manner appropriate for use relative to the base element, the second antenna can be positioned on a dorsal side and/or on a parietal bone of the patient. Accordingly, the local coil according to the disclosure advantageously enables magnetic resonance signals to be received from a greater volume, in particular from a jaw region and/or a dorsal region of the head of the patient.

The magnetic resonance apparatus according to the disclosure comprises a local coil according to an above-described variant. In a preferred variant, the local coil is mechanically connected to a patient table and/or a patient support and positioning apparatus of the magnetic resonance apparatus. The local coil may in particular comprise a positioning unit which is embodied to position the local coil relative to the magnetic resonance apparatus and/or a patient. The local coil comprises at least one antenna, a base element, a holding element, a first guide mechanism, a second guide mechanism and a safety mechanism according to an above-described variant. The magnetic resonance apparatus is embodied to acquire magnetic resonance data from a diagnostically relevant body region of a patient by means of the local coil.

In a variant, the magnetic resonance apparatus comprises a control unit that is connected by means of a signal connection to a drive for an actuating element of the safety mechanism. The control unit is preferably embodied to transmit information relating to the progress of a magnetic resonance measurement to a control unit of the drive by means of the signal connection. However, it is also conceivable that the control unit is embodied to transmit a control signal to the drive. The drive is preferably embodied to transmit a force onto an actuating element which is mechanically connected to the holding element or to the at least one antenna of the local coil. The safety mechanism can, therefore, ensure that a relative positioning of the holding element in the direction of the base element is avoided if a relative position of the at least one antenna deviates from a predetermined position of the at least one antenna relative to the holding element. It is equally conceivable that the safety mechanism is embodied to transfer the at least one antenna into a predetermined position relative to the holding element when the holding element is positioned in a predetermined position relative to the base element. In a further example, the safety mechanism may be further embodied to enable a positioning of the at least one antenna relative to the holding element when the holding element is positioned in a predetermined position relative to the base element.

The magnetic resonance apparatus according to the disclosure shares the advantages of the local coil according to the disclosure.

BRIEF DESCRIPTION OF THE DRAWINGS

Further advantages and details will become apparent from the following description of exemplary aspects taken in conjunction with the schematic drawings, in which.

DETAILED DESCRIPTION

Figure 1:
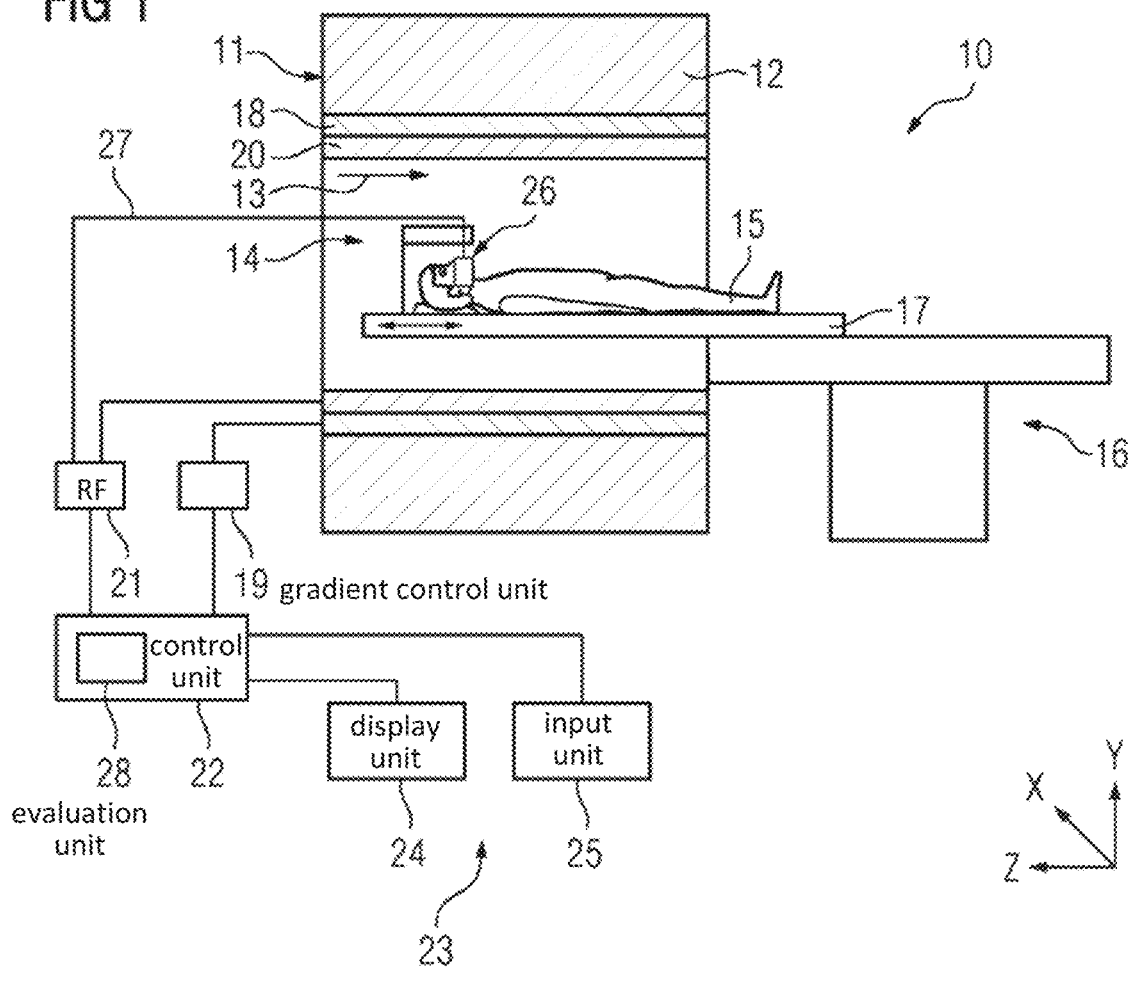
FIG. 1 shows a schematic representation of a variant of a magnetic resonance apparatus according to the disclosure.

FIG. 1 schematically shows a possible variant of a magnetic resonance apparatus 10 according to the disclosure comprising a local coil 26 according to the disclosure. The magnetic resonance apparatus 10 comprises a magnet unit 11 which has, e.g., a permanent magnet, an electromagnet or a superconducting main magnet 12 for generating a strong and in particular homogeneous basic magnetic field 13 (B0 magnetic field). The magnetic resonance apparatus 10 further comprises a patient receiving zone 14 for accommodating a patient 15. In the present exemplary aspect, the patient receiving zone 14 is embodied in the shape of a cylinder and is surrounded by the magnet unit 11 in a circumferential direction. Basically, however, aspects of the patient receiving zone 14 differing from this example are also conceivable.

The patient 15 can be positioned in the patient receiving zone 14 by means of a patient support and positioning apparatus 16 of the magnetic resonance apparatus 10. For this purpose, the patient support and positioning apparatus 16 has a patient table 17 embodied as movable inside the patient receiving zone 14. The magnet unit 11 additionally has a gradient coil 18 for generating magnetic gradient fields which is used for spatial encoding during a magnetic resonance measurement. The gradient coil 18 is controlled by means of a gradient control unit 19 of the magnetic resonance apparatus 10. The magnet unit 11 may further comprise a radiofrequency antenna which in the present exemplary aspect is embodied as a bodycoil 20 permanently integrated in the magnetic resonance apparatus 10. The bodycoil 20 is designed for the purpose of exciting atomic nuclei located in the basic magnetic field 13 generated by the main magnet 12. The bodycoil 20 is driven by a radiofrequency unit 21 of the magnetic resonance apparatus 10 and radiates radiofrequency signals into an examination space substantially formed by a patient receiving zone 14 of the magnetic resonance apparatus 10. The bodycoil 20 may furthermore be embodied also to receive magnetic resonance signals.

The magnetic resonance apparatus 10 comprises a control unit 22 for controlling the main magnet 12, the gradient control unit 19 and the radiofrequency unit 21. The control unit 22 is embodied for controlling the execution of a sequence such as e.g. an imaging gradient echo sequence, a TSE sequence or a UTE sequence. The control unit 22 further comprises an evaluation unit 28 for evaluating digitized magnetic resonance signals acquired during a magnetic resonance measurement.

The magnetic resonance apparatus 10 further comprises a user interface 23 which has a signal connection to the control unit 22. Control information such as, for example, imaging parameters and reconstructed magnetic resonance images can be displayed for a user on a display unit 24, for example on at least one monitor of the user interface 23. The user interface 23 also has an input unit 25 by means of which magnetic resonance imaging parameters can be entered by the user.

The magnetic resonance apparatus 10 further comprises a local coil 26 which in the present case is positioned on the head of the patient 15 and transmits magnetic resonance signals from a volume of a jaw region to the magnetic resonance apparatus 10. The local coil 26 preferably has an electric connection cable 27 which provides a signal connection to the radiofrequency unit 21 and the control unit 22. However, the local coil 26 can also be connected to the magnetic resonance apparatus 10 by means of a wireless signal connection. Like the bodycoil 20, the local coil 26 can also be embodied for exciting atomic nuclei and for receiving magnetic resonance signals. A transmit unit of the local coil 26 is driven by the radiofrequency unit 21 for the purpose of transmitting radiofrequency signals. On its outer circumference, the local coil 26 can enclose the head of the patient 15 along a longitudinal axis of the patient 15. The transmit unit and/or a receive unit of the local coil 26 can be carried in particular by a holding element 33 which can be positioned relative to a base element of the local coil 26.

The magnetic resonance apparatus 10 shown may of course comprise further components which are typically included in magnetic resonance apparatuses. It is also conceivable that, instead of the cylindrical design, the magnetic resonance apparatus 10 has magnetic-field-generating components arranged in a C-shaped, triangular or asymmetric configuration. The magnetic resonance apparatus 10 may in particular be a dedicated magnetic resonance apparatus 10 which is embodied to perform a magnetic resonance imaging scan of the jaw region of a standing or sitting patient 15.

Figure 2:
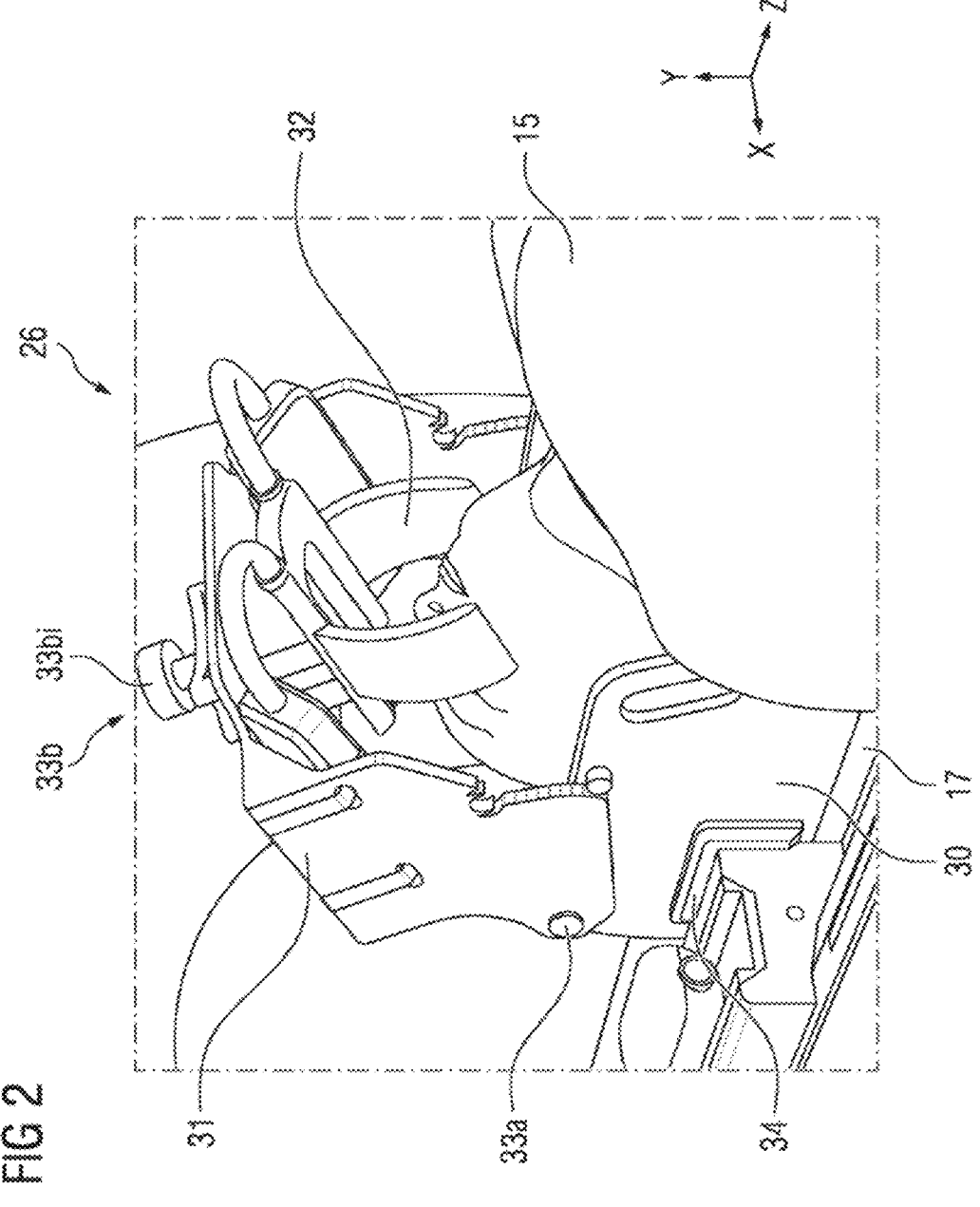
FIG. 2 shows a schematic representing a variant of a local coil according to the disclosure.

FIG. 2 shows a variant of the local coil 26 according to the disclosure in which the holding element 31 is pivotably mounted relative to the base element 30 and/or a positioning unit 34. For this purpose, the guide mechanism 33*a* has a pivot bearing. By means of the pivoting mechanism, the holding element 31 can be swiveled or tilted relative to the patient table 17 and/or the patient 15 around a pivotal point which is defined by a position or an axis of the pivot bearing.

The positioning unit 34 is embodied to position the local coil 26 relative to the patient support and positioning apparatus 16 and/or the patient 15. The positioning unit 34 can have e.g. a linear guide, a rail system and/or a comparable guide mechanism for this purpose. The positioning unit 34 is mechanically connected to the base element 30, which is connected in turn to the holding element 31 by means of the guide mechanism 33*a*.

The holding element 31 has a guide mechanism 33*b* which enables a carrier structure comprising the antenna 32 (hereinafter just antenna 32) to move relative to the holding element 31. The guide mechanism 33*b* is embodied to position the antenna 32 along a guide axis which, when the local coil 26 is positioned in a manner appropriate for use on the jaw region of the patient 15, i.e. for example in a snapped-shut state of the holding element 31, is aligned substantially parallel to a line of intersection of a sagittal plane and a transverse plane of the patient 15.

In a variant, the guide mechanism 33*b* can have pins or bolts which are fed through the holding element 31 and are mechanically connected to the antenna 32. In the present example, the guide mechanism 33*b* is embodied to position the antenna 32 along the Y-direction when the screw 33*bi* is turned. The bolts or pins of the guide mechanism 33*b* can in this case be guided e.g. through slotted holes in the holding element 31 so that the antenna 32 can also be positioned relative to the patient 15 along the Z-direction.

In the example shown in FIG. 2, the antenna 32 is embedded into a carrier structure which can be shaped to conform to a contour of a surface of the head of the patient 15. Preferably, the carrier structure is additionally embodied to protect the patient 15 against electrical voltages and/or a buildup of heat due to the antenna 32. The antenna 32 can have a plurality of antennas or signal conductors which are arranged adjacent to one another or partially overlapping in the carrier structure.

In a variant, the base element 30 of the dental coil 26, as shown in FIG. 2, has a storage element. The storage element can be embodied for example as a cushion or a comparable elastic element which adapts to a shape of a dorsal side of the head of the patient 15. The storage element preferably has a second antenna (not shown) which is positioned on the dorsal side of the head of the patient 15 when the patient 15 is positioned in a manner appropriate for use relative to the base element 30. The second antenna can be electrically connected to the antenna 32 or electrically separated from the latter.

Figure 3:
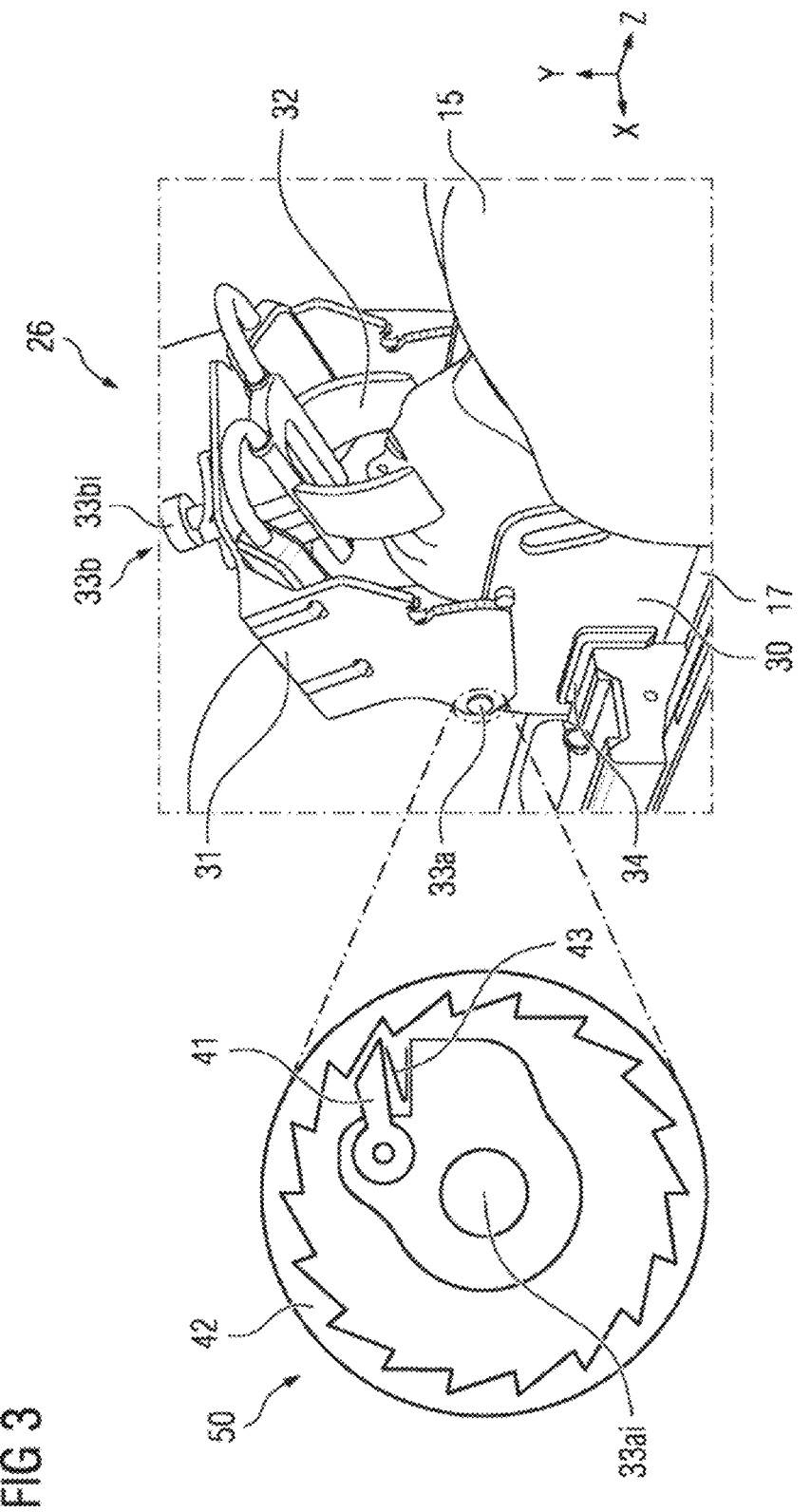
FIG. 3 shows a possible variant of a safety mechanism of a local coil according to the disclosure.

FIG. 3 shows a possible variant of the safety mechanism 50 which in the present example is integrated into the guide mechanism 33*a*. In the present case the pivot bearing has a latching element 41 (e.g., a first latching component) which is embodied to engage in the serrated profile 42 (e.g., a second latching component) during a closing movement of the holding element 31 in order to prevent or interrupt a closing movement of the holding element 31, i.e., a relative movement of the holding element 31 in the direction of the base element 30. For this purpose, the latching element 41 can be mechanically connected to a shaft 33*ai* of the pivot bearing shown. Accordingly, the serrated profile 42 can be integrated in the holding element 31 in such a way that it encloses the shaft 33*ai* of the pivot bearing along a circumferential direction on the outer circumference. Different variants and variations of the safety mechanism 50 are of course conceivable but are not to be discussed in detail here. In one example, the serrated profile 42 can also be embodied in the shaft 33*ai*, while the latching element 41 is positioned at a section of the holding element 31 and/or of the base element 30 which encloses the shaft along a circumferential direction on the outer circumference.

In the example shown, the latching element 41 is mechanically coupled to the guide mechanism 33*b* by means of a retaining element 43. The retaining element 43 may comprise e.g. a spring which is compressed or transferred into a no-load position as a result of a positioning of the antenna 32 in a predetermined position relative to the holding element 31. As shown in FIG. 3, the latching element 41 is mounted on the retaining element 43 and in the no-load position is mechanically separated from the serrated profile 42. If, on the other hand, the antenna 32 is not located in the predetermined position relative to the holding element 31, then the retaining element 43 remains in a holding position, as shown in the present example, and deflects the latching element 41 in the direction of the serrated profile 42. This causes the latching element 41 to engage in the serrated profile 42 and prevent a closing movement of the holding element 31 relative to the base element 30. The retaining element 43 is preferably embodied as a spring which can be elastically deformed during an opening movement of the holding element 31 relative to the base element 30 such that the latching element 41 can pass individual stop points of the serrated profile 42.

Figure 4:
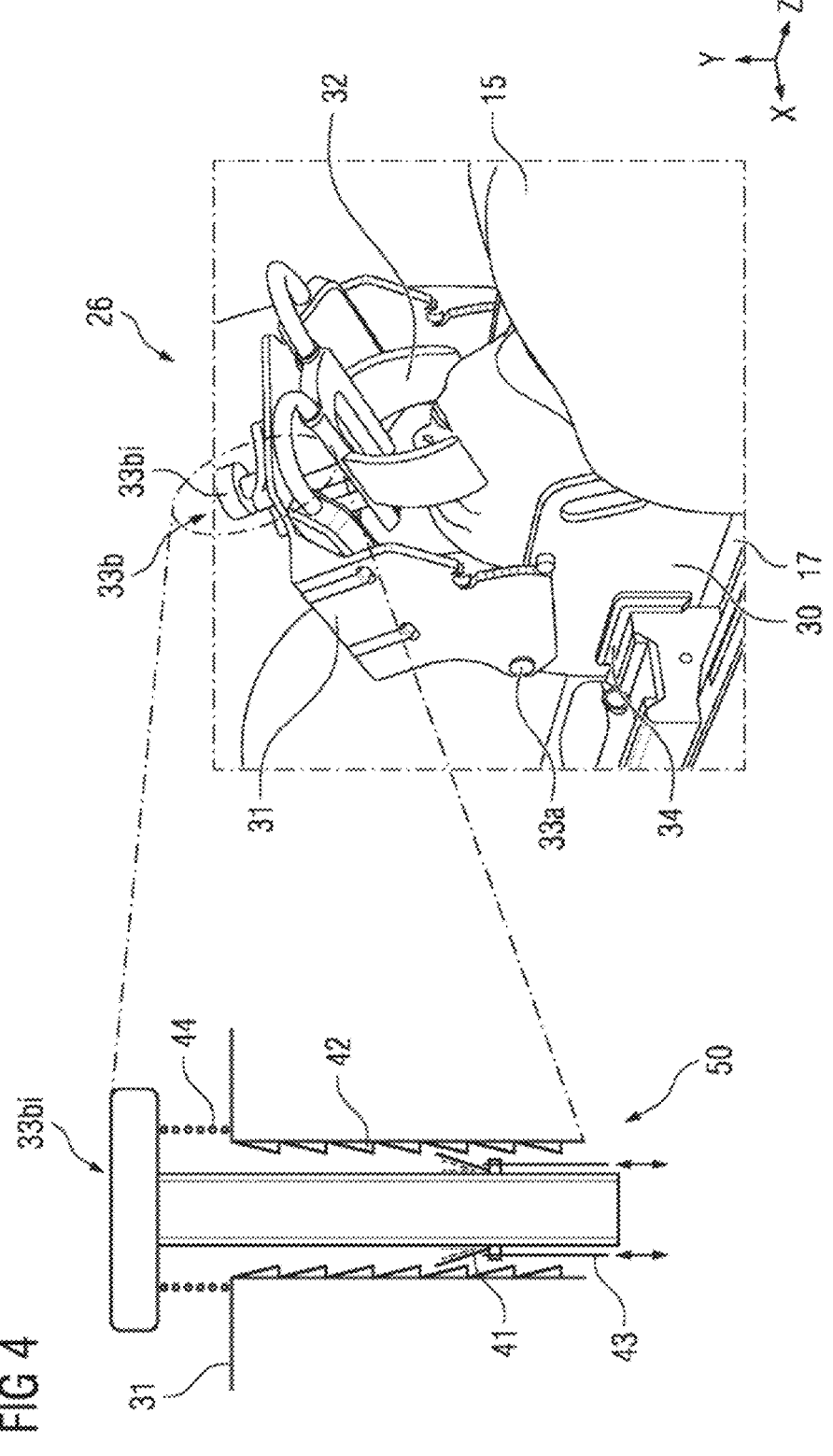
FIG. 4 shows a possible variant of a safety mechanism of a local coil according to the disclosure.

FIG. 4 shows a variant of the local coil 26 according to the disclosure in which the guide mechanism 33*b* has a clamping element 44. In the present example, the clamping element 44 is implemented as a mechanical spring which is connected to a manual actuating part 33*bi* and a surface of the holding element 31. The manual actuating part 33*bi* is mechanically connected to the antenna 32 and is embodied to move the antenna 32 relative to the holding element 31. During a relative movement of the antenna 32 in the direction of the base element 30 by means of the manual actuating part 33*bi*, the clamping element 44 is compressed and exerts a force acting in the opposite direction to the base element 30 onto the manual actuating part 33*bi* with the antenna 32.

In the present example, the guide mechanism 33*b* comprises a substantially cylindrical bore which has a serrated profile 42 (e.g. a second latching component) on its inside. The safety mechanism 50 has a latching element 41 (e.g. a first latching component) which is embodied to engage in the serrated profile 42 and prevent a movement of the manual actuating part 33*bi* and the antenna 32 in a direction facing away from the base element 30. This can make it easier for the user to position the antenna 32 in the position appropriate for use on the jaw region of the patient 15 since the manual actuating part 33*bi* is already locked in place when the antenna 32 is guided in the direction of the patient 15 in increments predefined by the serrated profile 42.

As shown in FIG. 3, the latching element can be mounted on a spring which is embodied to deflect the latching element 41 in the direction of the serrated profile 42. In the present example, the safety mechanism 50 further comprises a retaining element 43 which is mounted so as to be movable inside the cylindrical bore and is embodied to separate the latching element 41 mechanically from the serrated profile 42. The retaining element 43 can be mechanically connected to a manual switch or lever which permits the user to actuate the retaining element 43 manually in order to move the antenna 32 relative to the holding element 31 in a direction facing away from the base element 30. Preferably, however, the retaining element 43 is mechanically coupled to the guide mechanism 33*a*. The mechanical coupling between the retaining element 43 and the guide mechanism 33*a* can be embodied in such a way that the retaining element 43 is deflected in the direction of the latching element 41 and separates the latter mechanically from the serrated profile 42 when the holding element 31 is moved relative to the base element 30 into a position facing away from the patient support and positioning apparatus (i.e. an open position).

Figure 5:
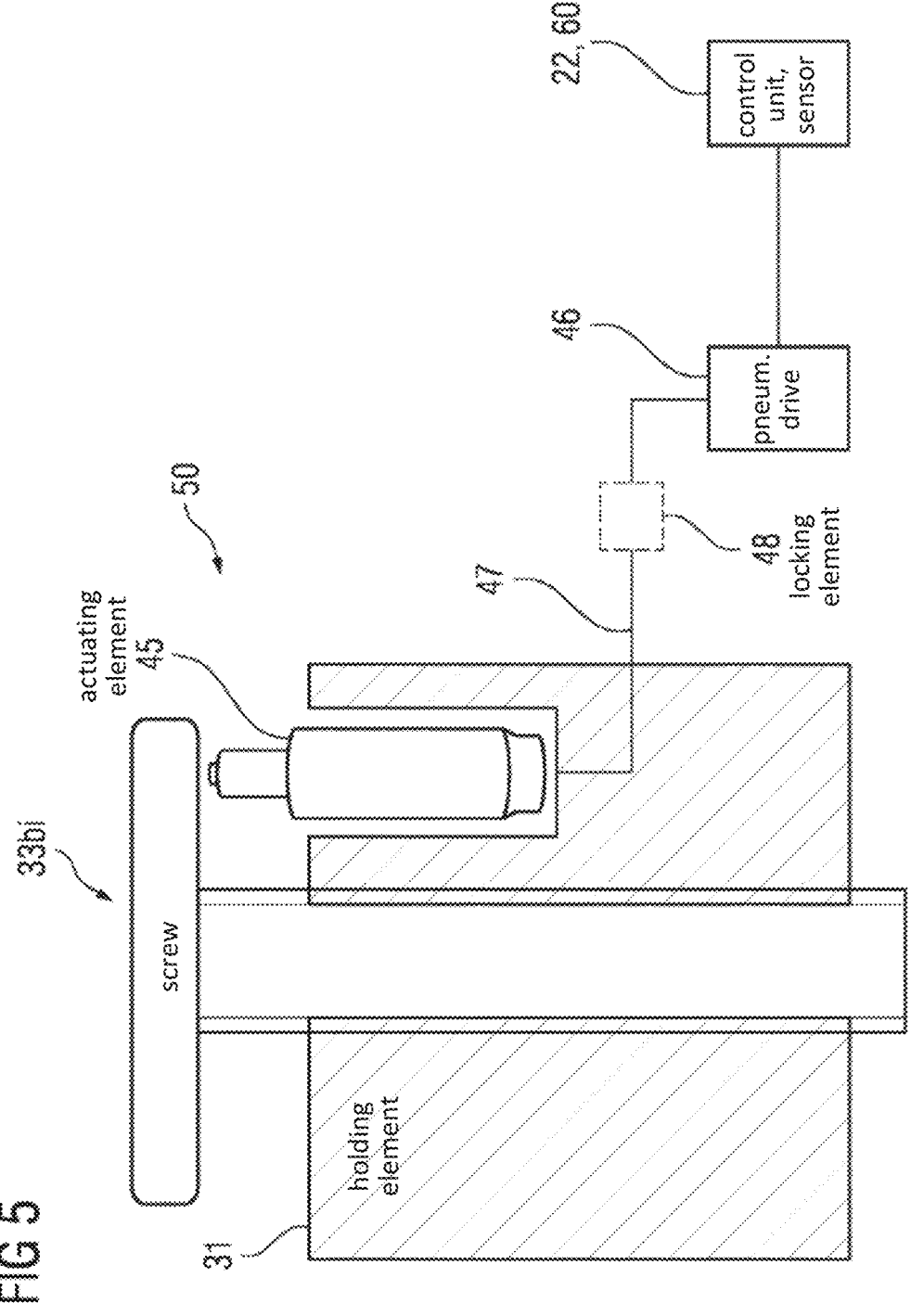
FIG. 5 shows a possible variant of a safety mechanism of a local coil according to the disclosure.

FIG. 5 shows a variant of the local coil 26 according to the disclosure in which the safety mechanism 50 comprises an actuating element 45 embodied as a compression spring with a drive 46. The drive 46 can, as shown, be embodied as a pneumatic drive, but also as an electric or a hydraulic drive. The actuating element 45 is embodied to transmit a force onto the manual actuating part 33*bi* of the guide mechanism 33*b*. In the present example, the force is aligned in an opposite direction to the base element 30 and/or the patient 15 such that a movement of the antenna 32 in a direction facing toward the base element 30 by means of the guide mechanism 33*b* is made difficult or is prevented. In this case the pneumatic drive 46 has a signal connection to a sensor 60 and/or to the control unit 22 of the magnetic resonance apparatus 10. In a variant, the pneumatic drive 46 or a control unit (not shown) of the pneumatic drive 46 is embodied to sense a signal by means of the signal connection, which signal comprises information relating to a predetermined position of the holding element 31 relative to the base element 30. The information concerning the predetermined position of the holding element 31 relative to the base element 30 may for example comprise information relating to a reaching of an end position, a current position of the holding element 31 relative to the base element 30 and/or information relating to an execution sequence of a magnetic resonance measurement. The sensor 60 can be implemented for example as a distance sensor, an incremental position encoder, a position encoder, a contactor or the like. Preferably, the sensor 60 is embodied to determine a presence of the holding element 31 in a predetermined position relative to the base element 30 (and/or a corresponding configuration of the guide mechanism 33*a*).

In a further variant, a signal connection to the control unit 22 and/or to a sensor 60 can be dispensed with. In this case the drive 46 has a locking element 48 which is embodied to inhibit the fluidic connection 47 to the actuating element 45 when the holding element 31 is located in a predetermined position relative to the base element 30. The locking element 48 can be embodied as a valve, for example. The guide mechanism 33*a* is In an alternative a variant, the actuating element 45 is embodied to transfer the antenna 32 into a starting position or a predetermined relative position with respect to the holding element 31. For this purpose, the actuating element 45 can in particular also be integrated in the cylindrical bore of the holding element 31 and can transmit a rotational movement and/or a translational movement onto the actuating part 33*bi*. In this case the drive 46 is preferably embodied as an electric drive which positions the antenna 32 in accordance with the information relating to the predetermined position of the holding element 31 relative to the base element 30. It is furthermore conceivable to dispense with an implementation of a locking element 48. In this case the actuating element 45 and the drive 46 can be embodied to transfer the antenna 32 into the predetermined position relative to the holding element 31 automatically in accordance with a signal of the sensor 60 and/or the control unit 22. It is further conceivable that the actuating element 45 and the drive 46 are embodied to position the antenna 32 relative to the holding element 31 automatically or by remote control by a user.

Figure 6:
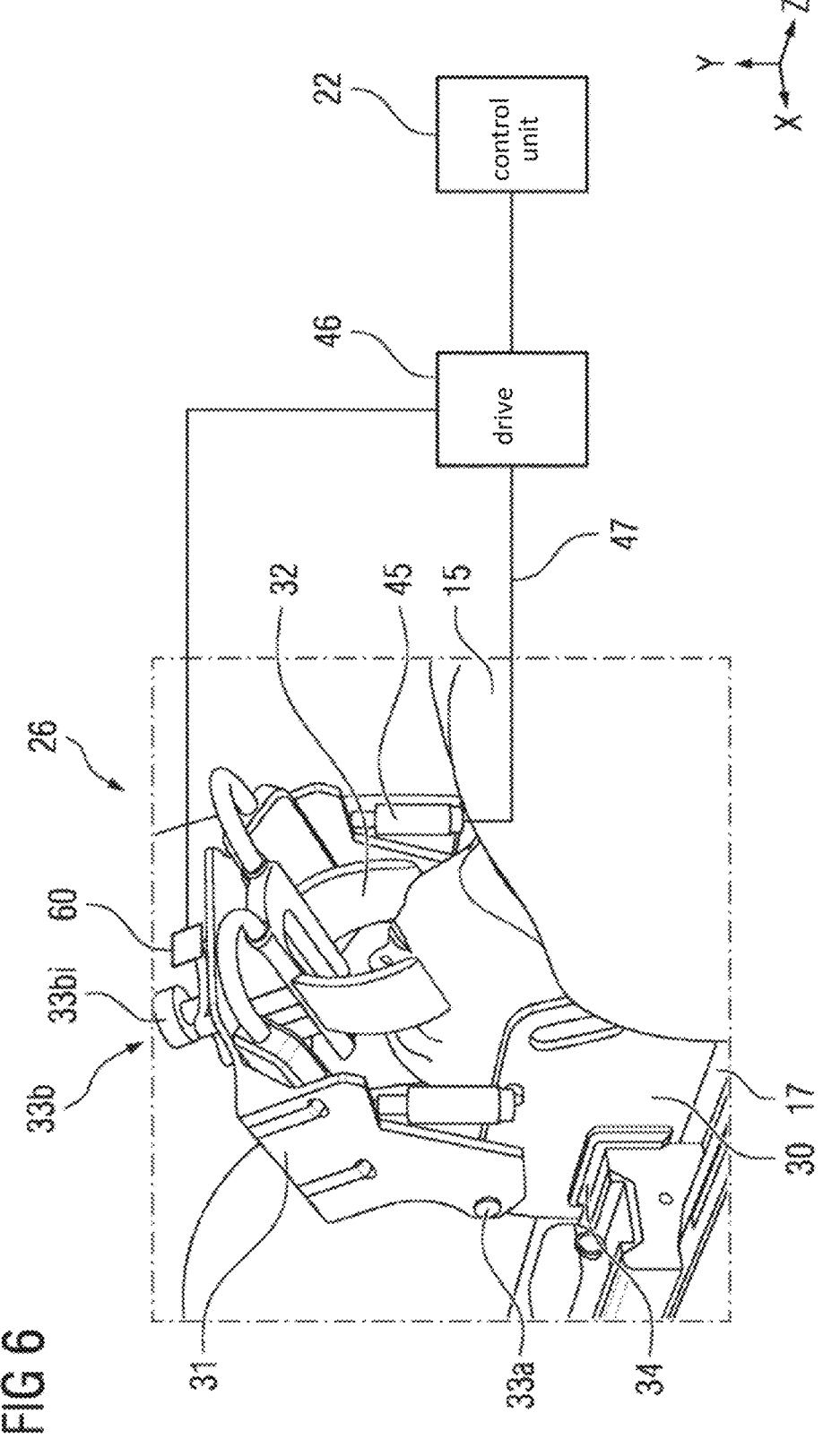
FIG. 6 shows a possible variant of a safety mechanism of a local coil according to the disclosure.

FIG. 6 shows a further possible a variant of the local coil 26 according to the disclosure in which the safety mechanism 50 comprises an actuating element 45. In the present example, the actuating element 45 is implemented as a compression spring to which a pressure is applied by a drive 46. The pressure is preferably sufficiently high to prevent a manual transfer of the holding element 31 into the closed position.

The drive 46 has a signal connection to a sensor 60 and/or to the control unit 22 of the magnetic resonance apparatus 10. The sensor 60 can be implemented for example as a distance sensor, an incremental position encoder, a position encoder, a contactor or the like which is embodied to detect a presence of the antenna 32 in a predetermined position relative to the holding element 31 (and/or a corresponding configuration of the guide mechanism 33*b*). If such a predetermined position of the antenna 32 relative to the holding element 31 is present, the sensor 60 relays a signal to the drive 46. If such a signal of the sensor 60 is present, the drive 46 is accordingly embodied to adjust an action of force exerted onto the compression spring so that the holding element 31 can be transferred manually into the closed position. The drive can for example be embodied to open a valve (cf. FIG. 5) to a bypass or to manipulate a pressure in a line of the fluidic connection 47. It is also conceivable that, instead of or in addition to the sensor 60, the drive 46 has a signal connection to the control unit 22 of the magnetic resonance apparatus 10. According to an above-described a variant, the drive 46 can in this case be embodied to adjust the action of force exerted onto the compression spring as a function of a progress of the magnetic resonance measurement.

The drive 46 in FIG. 6 can of course also be embodied as an electric drive which is designed to limit a movement of the holding element 31 relative to the base element 30 in accordance with the predetermined position of the antenna 32 relative to the holding element 31. It is further conceivable for an opening movement and/or a closing movement of the holding element 31 by means of the drive 46 to be automated. For example, an opening and/or closing of the holding element 31 relative to the base element 30, but also a relative movement of the antenna 32 into a safety position (which excludes an injury to the patient), can be accomplished in accordance with a signal of the sensor 60 and/or the control unit 22.

Figure 7:
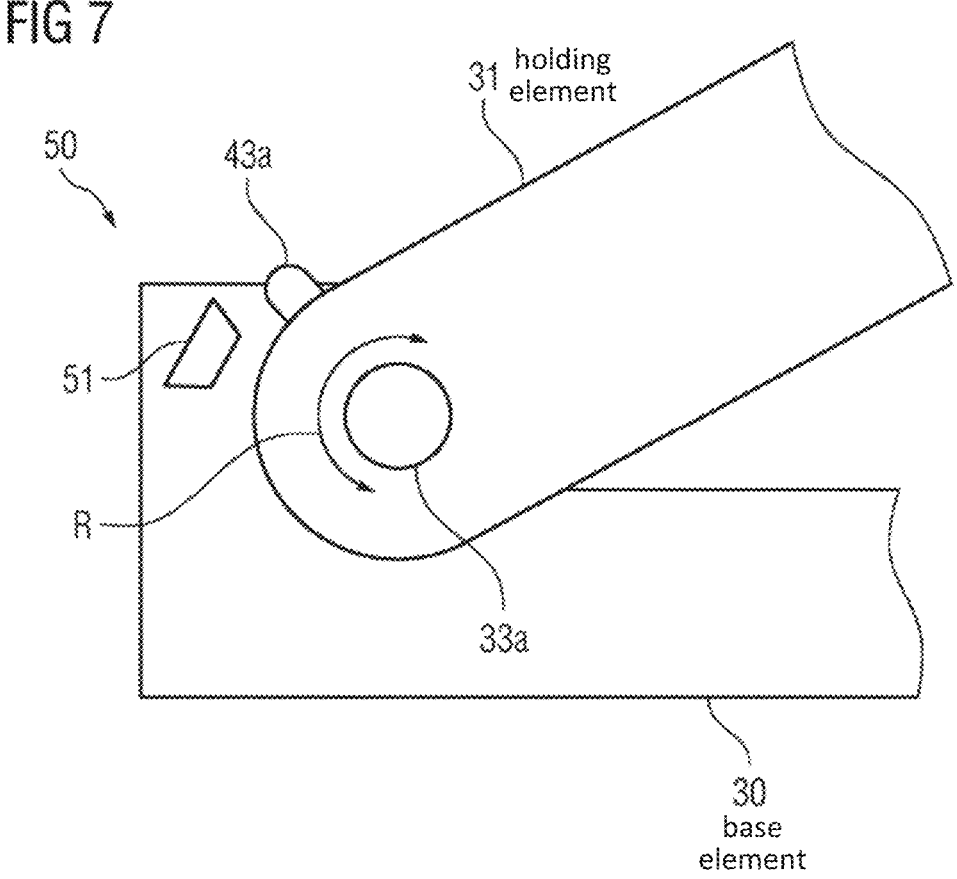
FIG. 7 shows a possible variant of a safety mechanism of a local coil according to the disclosure.

FIG. 7 shows a variant of the local coil 26 according to the disclosure according to FIG. 4. In the present example, the retaining element 43 has a nipple 43*a* which is mechanically coupled to the retaining element 43 according to FIG. 4. During an opening movement of the holding element 31, the nipple 43*a* is guided against a stop element 51 and moved relative to the holding element 31 along the direction of rotation R. The movement or tilting of the nipple 43*a* causes a deflection of the retaining element 43, as a result of which the latching element 41 is mechanically separated from the serrated profile 42 and the manual actuating part 33*bi* is moved by means of the clamping element 44 in the direction facing way from the base element 30. The safety mechanism 50 can of course also be implemented in such a way that the mechanical separation of the latching element 41 from the serrated profile 42 is effected by a closing movement of the holding element 31.

Although the disclosure has been illustrated and described in more detail on the basis of the preferred exemplary aspects, the disclosure is nonetheless not limited by the disclosed examples and other variations can be derived herefrom by the person skilled in the art without leaving the scope of protection of the disclosure.

The invention claimed is:

1. A local coil, comprising:

at least one antenna embodied to receive radiofrequency signals in a frequency range and power range of a magnetic resonance measurement;

a base element;

a holding element, wherein the at least one antenna is mechanically connected to the holding element, and the base element is embodied to hold the holding element together with the at least one antenna in a position appropriate for use on a diagnostically relevant body region of a patient;

a first guide mechanism mechanically connected to the base element and the holding element, and embodied to position the holding element variably relative to the base element;

a second guide mechanism mechanically connected to the holding element and the at least one antenna, and embodied to position the at least one antenna variably relative to the holding element; and a safety mechanism embodied to prevent a collision of the at least one antenna with the patient during a transfer of the holding element from an open position into a closed position using the first guide mechanism.

2. The local coil of claim 1, wherein the safety mechanism is embodied to prevent a collision of the at least one antenna with the diagnostically relevant body region of the patient during the transfer of the holding element from the open position into the closed position using the first guide mechanism.

3. The local coil of claim 1, wherein the safety mechanism is embodied to limit a movement of the holding element using the first guide mechanism when the holding element is transferred from the open position into the closed position as a function of a safety position of the at least one antenna relative to the holding element.

4. The local coil of claim 3, wherein the safety mechanism has a first latching component, which is embodied to engage in a second latching component of the first guide mechanism and to prevent the holding element from being transferred from the open position into the closed position, and wherein the first latching component is mechanically connected to a retaining element, and is separable using the retaining element manually or automatically from the second latching component of the first guide mechanism in order to enable the holding element to be transferred from the open position into the closed position.

5. The local coil of claim 4, wherein the first latching component is mechanically coupled to the second guide mechanism using the retaining element, and is mechanically separable from the second latching component of the first guide mechanism using a movement of the at least one antenna into a predetermined position relative to the holding element using the second guide mechanism in order to enable the holding element to be transferred from the open position to the closed position.

6. The local coil of claim 1, wherein the safety mechanism is mechanically coupled to the first guide mechanism and the second guide mechanism and is embodied to transfer the at least one antenna into a safety position using kinematic energy of a movement of the holding element relative to the base element.

7. The local coil of claim 6, wherein the second guide mechanism has a clamping element that is embodied to be elastically deformed following a movement of the at least one antenna relative to the holding element in a direction of the base element and to transmit a force acting opposite to the movement onto the at least one antenna, wherein the safety mechanism has a first latching component that is mechanically connected to the at least one antenna and is embodied to engage in a second latching component of the second guide mechanism and counteract the force of the clamping element, and wherein the first latching component is mechanically coupled to the first guide mechanism, and is separable mechanically from the second latching component of the second guide mechanism using a predetermined movement of the holding element relative to the base element in order to enable a deflection of the at least one antenna in a direction facing away from the base element using the clamping element.

8. The local coil of claim 1, wherein the safety mechanism comprises an actuating element, which is embodied to transmit a force onto the at least one antenna in order to deflect the at least one antenna relative to the holding element in a direction facing away from the base element, and wherein the local coil further comprises a locking element, which is mechanically coupled to the first guide mechanism and is embodied to interrupt transmission of the force onto the at least one antenna using the actuating element when the base element and the holding element are located in a predetermined relative position.

9. The local coil of claim 1, wherein the safety mechanism comprises an actuating element, wherein the actuating element is embodied to transmit a force onto the holding element to limit a movement of the holding element relative to the base element and/or to deflect the holding element in a direction facing away from the base element, and wherein the local coil further comprises a locking element, which is mechanically coupled to the second guide mechanism and is embodied to interrupt transmission of the force onto the holding element using the actuating element when the at least one antenna is located in a predetermined position relative to the holding element.

10. The local coil of claim 8, wherein the actuating element has a fluidic connection to a pneumatic and/or hydraulic drive, and wherein the locking element is embodied to interrupt the fluidic connection between the actuating element and the pneumatic and/or hydraulic drive.

11. The local coil of claim 1, wherein the safety mechanism comprises an actuating element having a drive, wherein the actuating element is mechanically connected to the at least one antenna or the holding element, and wherein the drive is embodied to deflect the at least one antenna or the holding element using the actuating element in a direction facing away from the base element as a function of a control signal.

12. The local coil of claim 1, wherein the first guide mechanism and/or the second guide mechanism are/is embodied as a linear guide, a telescopic guide, a joint, a hinge, or a push-fit system.

13. The local coil of claim 12, wherein the first guide mechanism has a pivoting mechanism, wherein the holding element is mounted to be pivotable using the pivoting mechanism through a maximum angle relative to the base element, wherein the open position is characterized by the maximum angle between the base element and the holding element, and wherein the maximum angle is chosen such that a head of the patient can be positioned unobstructed in a position appropriate for use relative to the local coil.

14. The local coil of claim 1, further comprising:

a second antenna mechanically connected to the base element and positioned on a side of the patient facing away from the at least one antenna when the patient is positioned in a manner appropriate for use relative to the base element.

15. A magnetic resonance apparatus comprising:

the local coil of claim 1, wherein the magnetic resonance apparatus is embodied to acquire magnetic resonance data of a diagnostically relevant body region of a patient using the local coil.

* * * * *